(12) United States Patent
Maher et al.

(10) Patent No.: US 9,702,823 B2
(45) Date of Patent: Jul. 11, 2017

(54) OPTICAL SYSTEMS AND METHODS FOR BIOLOGICAL ANALYSIS

(71) Applicant: LIFE TECHNOLOGIES CORPORATION, Carlsbad, CA (US)

(72) Inventors: Kevin Maher, Woodside, CA (US); Mingsong Chen, Singapore (SG); Jacob Freudenthal, San Jose, CA (US); Kuan Moon Boo, Singapore (SG); Soo Yong Lau, Singapore (SG); David Fortescue, San Francisco, CA (US); Ming Shen, Singapore (SG); Woon Liang Terence Soh, Singapore (SG)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 206 days.

(21) Appl. No.: 14/348,878

(22) PCT Filed: Sep. 28, 2012

(86) PCT No.: PCT/US2012/058107
§ 371 (c)(1),
(2) Date: Mar. 31, 2014

(87) PCT Pub. No.: WO2013/049709
PCT Pub. Date: Apr. 4, 2013

(65) Prior Publication Data
US 2014/0248693 A1    Sep. 4, 2014

Related U.S. Application Data

(60) Provisional application No. 61/541,453, filed on Sep. 30, 2011, provisional application No. 61/541,495, filed on Sep. 30, 2011.

(51) Int. Cl.
*G01N 21/64*        (2006.01)

(52) U.S. Cl.
CPC ..... *G01N 21/6486* (2013.01); *G01N 21/6428* (2013.01); *G01N 21/6452* (2013.01);
(Continued)

(58) Field of Classification Search
CPC ....... G01N 21/6452; G01N 2021/6471; G01N 2021/6478; G01N 21/6428; G01N 21/6486; G01N 2201/062
See application file for complete search history.

(56) References Cited

U.S. PATENT DOCUMENTS

| 4,920,386 A | 4/1990 | Tsuchiya et al. |
| 2005/0151972 A1 | 7/2005 | Boege et al. |

(Continued)

FOREIGN PATENT DOCUMENTS

| CN | 101793826 | 8/2010 |
| GB | 2197499 | 5/1988 |

(Continued)

OTHER PUBLICATIONS

11201401919T, SG—Search Report and Written Opinion mailed Jan. 28, 2016, 12 pages.

*Primary Examiner* — Nathan Bowers
*Assistant Examiner* — Lydia Edwards
(74) *Attorney, Agent, or Firm* — Jones Robb, PLLC (57) ABSTRACT

An instrument for processing and/or measuring a biological process contains an excitation source, a sample holder, an optical sensor, an excitation optical system, and an emission optical system. The sample holder is configured to receive a plurality of biological samples. The optical sensor is configured to receive an emission from the biological samples. The excitation optical system is disposed along an excitation optical path and is configured to direct the electromagnetic radiation from the excitation source to the biological samples. The emission optical system is disposed along an emission optical path and is configured to direct electromagnetic emissions from the biological samples to the optical sensor. The instrument further contains a plurality of filter assemblies configured to be interchangeably located along at least one of the optical paths. The plurality of filter components includes a first filter assembly characterized by a first optical power and a first filter having a first filter
(Continued)

function, the first filter function characterized by at least one of a first low-pass wavelength or a first high-pass wavelength. The second filter assembly is characterized by a second optical power and a second filter having a second filter function, the second filter function comprising at least one of a second low-pass wavelength that is different than the first low-pass wavelength or a second high-pass wavelength that is different than the first high-pass wavelength.

10 Claims, 6 Drawing Sheets

(52) U.S. Cl.
CPC ......... *G01N 2021/6471* (2013.01); *G01N 2021/6478* (2013.01); *G01N 2201/062* (2013.01)

(56) References Cited

U.S. PATENT DOCUMENTS

| | | | |
|---|---|---|---|
| 2006/0006067 A1* | 1/2006 | Unger | G02B 21/36 204/452 |
| 2006/0121602 A1 | 6/2006 | Hoshizaki et al. | |
| 2008/0117425 A1* | 5/2008 | Kain | C12Q 1/6837 356/455 |

FOREIGN PATENT DOCUMENTS

| WO | WO-01/35079 | 5/2001 |
|---|---|---|
| WO | WO-2007/031203 | 3/2007 |

* cited by examiner

FIG. 1

| Transmission – Emission Filters | | |
|---|---|---|
| Filter No. | Low-pass wavelength | High-pass wavelength |
| 1 | 510 nm | 530 nm |
| 2 | 548 nm | 568 nm |
| 3 | 576 nm | 596 nm |
| 4 | 613 nm | 633 nm |
| 5 | 672 nm | 692 nm |
| 6 | 700 nm | 720 nm |

FIG. 2

| Transmission – Excitation Filters | | |
|---|---|---|
| Filter No. | Low-pass wavelength | High-pass wavelength |
| 1 | 460 nm | 480 nm |
| 2 | 510 nm | 530 nm |
| 3 | 540 nm | 560 nm |
| 4 | 570 nm | 590 nm |
| 5 | 630 nm | 650 nm |
| 6 | 652 nm | 672 nm |

OPTICAL SYSTEMS AND METHODS FOR BIOLOGICAL ANALYSIS

CROSS-REFERENCE TO RELATED APPLICATIONS

This application is a 371 U.S. national phase of international application no. PCT/US2012/058107, filed Sep. 28, 2012, and claims the benefit of priority of U.S. provisional application Ser. No. 61/541,495, filed Sep. 30, 2011, and U.S. provisional application Ser. No. 61/541,453, filed on Sep. 30, 2011, which applications are incorporated herein by reference in their entirety.

BACKGROUND OF THE INVENTION

Field of the Invention

The present invention relates generally to systems, devices, and methods for observing, testing, and/or analyzing one or more biological samples, and more specifically to systems, devices, and methods comprising an optical system for observing, testing, and/or analyzing one or more biological samples.

Description of the Related Art

Optical systems for biological and biochemical reactions have been used to monitor, measure, and/or analyze such reactions in real time. Such systems are commonly used in sequencing, genotyping, polymerase chain reaction (PCR), and other biochemical reactions to monitor the progress and provide quantitative data. For example, an optical excitation beam may be used in real-time PCR (qPCR) reactions to illuminate hybridization probes or molecular beacons to provide fluorescent signals indicative of the amount of a target gene or other nucleotide sequence. Increasing demands to provide greater numbers of reactions per test or experiment have resulted in instruments that are able to conduct ever higher numbers of reactions simultaneously.

The increase in the number sample sites in a test or experiment has led to microtiter plates and other sample formats that provide ever smaller sample volumes. In addition, techniques such as digital PCR (dPCR) have increased the demand for smaller sample volumes that contain either zero or one target nucleotide sequence in all or the majority of a large number of test samples. The combination of small feature size (e.g., an individual sample site or volume) and large field of view to accommodate a large number of test samples has created a need for optical systems that provide high optical performance with relatively small sample signals.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE DRAWINGS

As used herein, the term "light" means electromagnetic radiation within the visible waveband, for example, electromagnetic radiation with a wavelength in a vacuum that is within a range from 390 nanometers to 780 nanometers. As used herein, the term "infrared" means electromagnetic radiation having a wavelength within a range of 0.74 micrometer to 300 micrometers.

As used herein, the term "optical power" means the ability of a lens or optic to converge or diverge light to provide a focus (real or virtual) when disposed within air. As used herein the term "focal length" means the reciprocal of the optical power. As used herein, the term "diffractive power" or "diffractive optical power" means the power of a lens or optic, or portion thereof, attributable to diffraction of incident light into one or more diffraction orders. Except where noted otherwise, the optical power of a lens, optic, or optical element is from a reference plane associated with the lens or optic (e.g., a principal plane of an optic).

As used here, the term "about zero" or "approximately zero" means within 0.1 of the unit of measure being referred to, unless otherwise noted. For example, "about zero meters" means less than or equal to 0.1 meters, if the dimension may only reasonably have a positive value, or within a range of −0.1 meters to +0.1 meters, if the dimension may have either a positive or negative value.

When used in reference to an optical power in units of Diopters, the terms "about" or "approximately", as used herein, means within 0.1 Diopter. As used herein, the phrase "about zero Diopter" or "approximately zero Diopter" means within a range of −0.1 Diopter to +0.1 Diopters.

Figure 1:
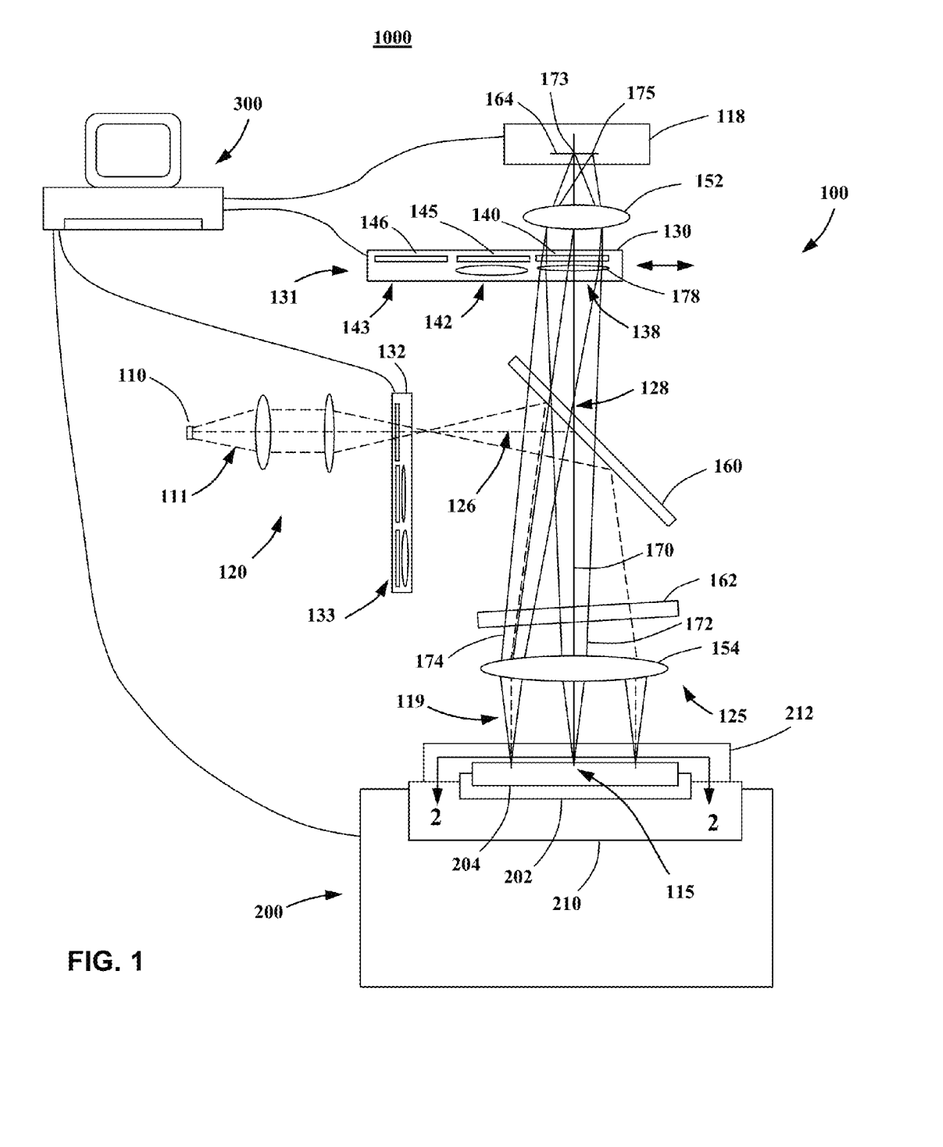
FIG. 1 is a schematic representation of a system according to an embodiment of the present invention.
Figure 2:
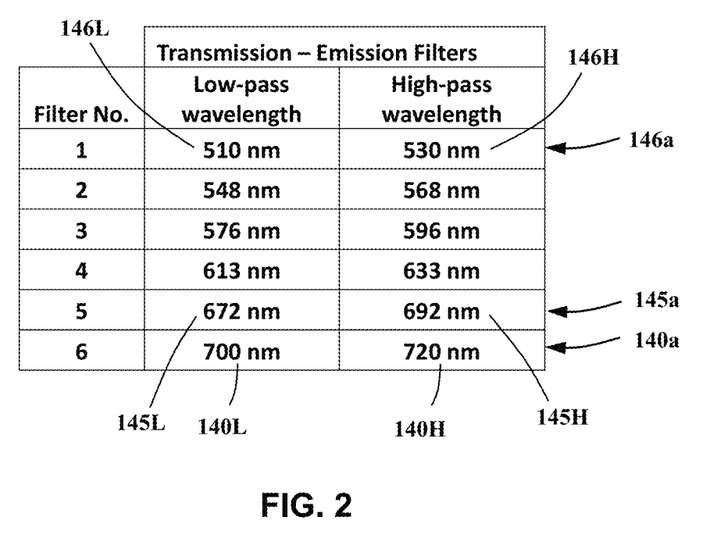
FIG. 2 is a table of the filter functions for a plurality of filter used in the emission filter assembly shown in FIG. 1
Figure 3:
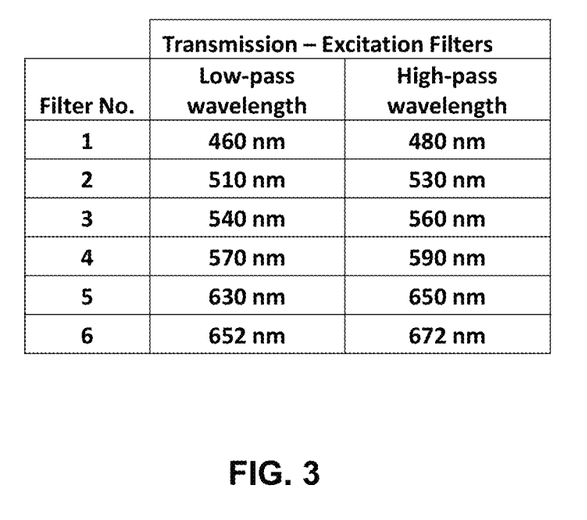
FIG. 3 is a table of the filter functions for a plurality of filter used in the excitation filter assembly shown in FIG. 1

Referring to FIGS. 1-3, a system or instrument 1000 for biological analysis comprises an optical system 100. In certain embodiments, system or instrument 1000 additionally comprises a sample block or processing system 200 and/or an electronic processor, computer, or controller 300 configured to control, monitor, and/or receive data from optical system 100 and/or sample processing system 200. Without limiting the scope of the present invention, system or instrument 1000 may be a sequencing instrument, a polymerase chain reaction (PCR) instrument (e.g., a real-time PCR (qPCR) instrument and/or digital PCR (dPCR) instrument), an instrument for providing genotyping information, or the like.

In certain embodiments, optical system 100 comprises an illumination or excitation source 110 providing one or more excitation beams 111 and an optical sensor 118 configured to receive one or more emission beams 119 from one or more biological samples 115. Optical system 100 also comprises an excitation optical system 120 and an emission optical system 125. Excitation optical system 120 is disposed along an excitation optical path 126 and is configured to direct the electromagnetic radiation or light from excitation source 110 to sample holder containing one or more biological samples. Emission optical system 125 is disposed along an emission optical path 128 and is configured to direct electromagnetic emissions from biological samples 115 to optical sensor 118, for example, one or more fluorescence signals produced at one or more wavelengths in response to the one or more excitation beams 111. Optical system 100 may further comprise an emission filter assembly 130 comprising a plurality of filter components, elements, or modules 131 configured to interchangeably locate or move one or more of filter modules 131 into emission optical path 128. Optical system 100 may additionally comprise an excitation filter assembly 132 comprising a plurality of filter components, elements, or modules 133, wherein excitation filter assembly 132 is configured to interchangeably locate or move one or more of filter modules 133 into excitation optical path 126. Optical system 100 may further comprise a first optical element 152 configured to direct light to optical sensor 118, a second optical element 154 configured to direct excitation light to, and/or emission light from, the biological samples, a beam-splitter 160, and/or one or more optical windows 162.

In certain embodiments, sample processing system 200 comprises a carrier or support frame 202 configured to receive a sample holder 204. Sample holder 204 comprises a plurality or array of cells 205 for containing a corresponding plurality or array of biological samples 115 that may be processed by sample processing system 200 and/or optical system 100. Cells 205 may be in the forms of sample wells, cavities, through-holes, or any other chamber type suitable containing and/or isolating the plurality of biological samples 115. For example, sample cells 205 may be in the form of sample beads in a flow cell or discrete samples deposited on top of a substrate surface such as a glass or silicon substrate surface.

Figure 4:
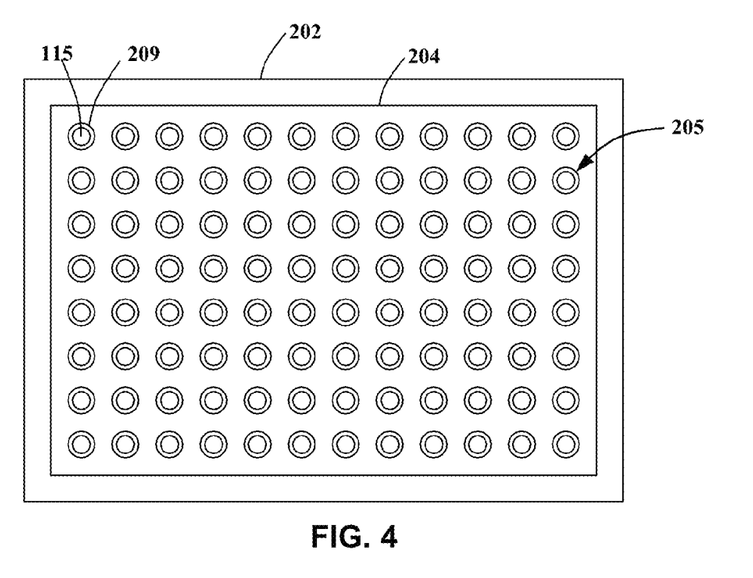
FIG. 4 is a top view of a sample holder and carrier according to an embodiment of the present invention.

With additional reference to FIG. 4, sample holder 204 comprises 96 sample cells 205 that are in the form of 96 sample wells 209 configured to provide 96 isolated or distinct biological samples 115. Alternatively, sample holder 204 may comprise less than 96 well and samples, for example, 48 wells and samples, or may contain more than 96 wells, for example, 384 or more wells and samples. In certain embodiments, carrier 202 is configured to receive more than one sample holder 204 for simultaneous processing by sample processing system 200 and/or optical system 100.

Sample processing system 200 may further comprise a block or assembly 210 for receiving sample holder 204. Block 210 may be thermal block including temperature control hardware for controlling or cycling the temperature of biological samples 115. Sample processor system 200 may further comprise a thermally controlled or heated lid 212 disposed about sample holder 204. Thermally controlled lid 212 may be configured to aid in controlling a thermal and/or humidity environment of biological samples 115 or sample holder 204, for example, to aid in preventing condensation from forming on samples 115 or optical elements of sample holder 204. In certain embodiments, system 200 includes a set of different types or configurations of block 210 and/or different types or configurations of thermally controlled lid 212, where each member of the set is configured for use with a different type or number of sample holders 204 or carriers 202.

Figure 5:
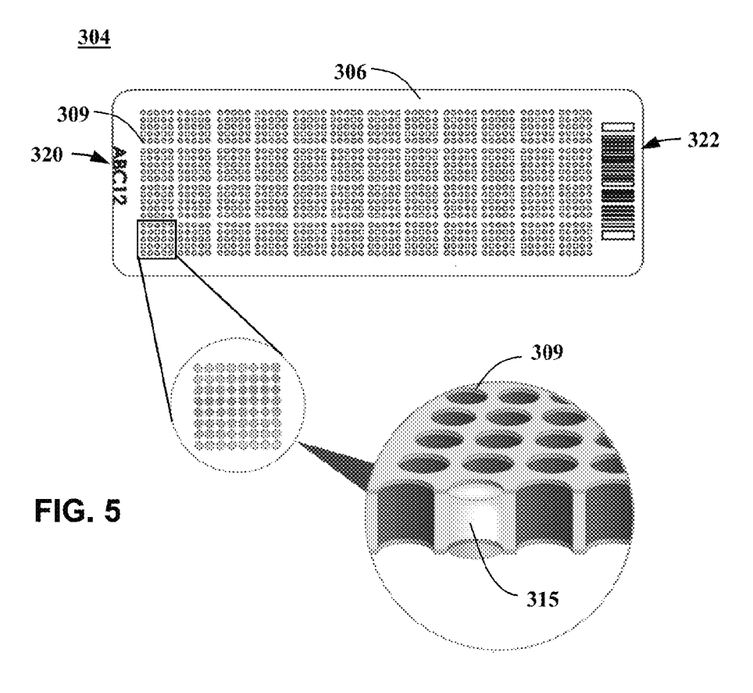
FIG. 5 is a top view and magnified views of a sample holder according to another embodiment of the present invention.
Figure 6:
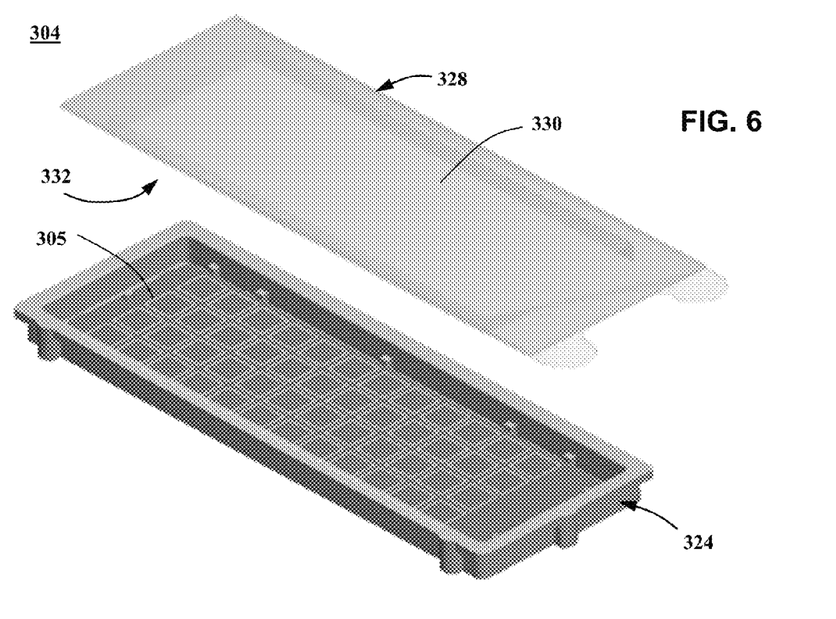
FIG. 6 is a perspective view of a sample holder according to yet another embodiment of the present invention.
Figure 7:
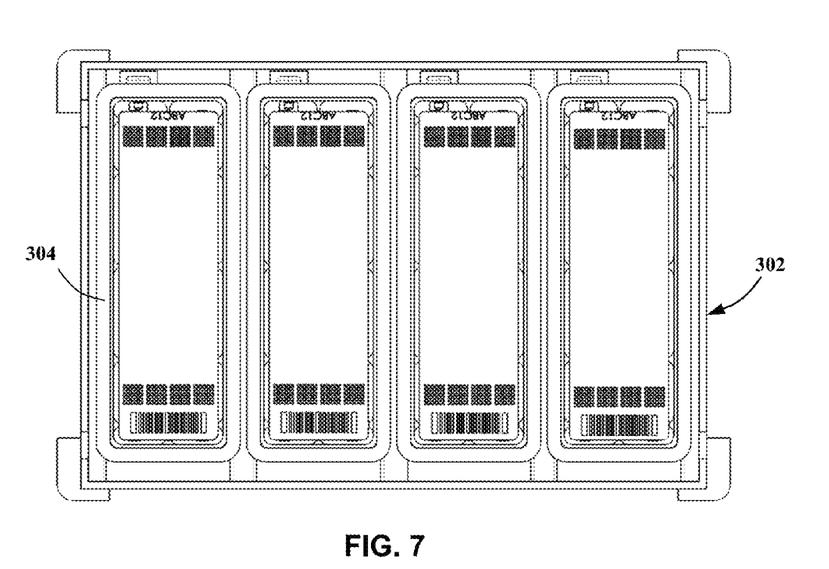
FIG. 7 is a top view of a sample holder and carrier according to another embodiment of the present invention.

Referring to FIG. 5, system 1000 may be additionally or alternatively configured to receive and process a sample holder 304 comprising a substrate 306 including a plurality of through-holes 309. In such embodiments, through-holes 309 are configured to maintain isolated or distinct biological samples 315 by capillary forces, for example, by forming through-holes to have an appropriately small diameter and/or through the use of hydrophilic and/or hydrophobic materials or coatings. Substrate 306 may further comprise an alphanumeric 320, a barcode 322, and/or similar symbol for identification or processing purposes. Referring to FIG. 6, sample holder 304 may further comprise an enclosure or case for protecting or sealing substrate 306 and the biological samples contained in through-holes 309. The case may comprise a base 324 and a cover 328 that are configured to seal substrate 306 between base 324 and cover 328, for example, to reduce or prevent evaporation of the biological samples. Cover 328 is made of a transmissive material and comprises a top surface 330 and an opposing bottom surface 332 for providing optical access to substrate 306. One or both surfaces 330, 332 may comprise an antireflective coating, for example, to reduce retro-reflections of light from excitation beam 111 back toward optical sensor 118. Additionally or alternatively, one or both surfaces 330, 332 may be disposed at an angle relative to a front surface of substrate 306, for example, to reduce retro-reflections of light from excitation beam 111 back toward optical sensor 118. Referring to FIG. 7, one or more sample holders 304 may be retained by or mounted on a carrier 302 that is configured to be received by sample processing system 200. In the illustrated embodiment shown in FIG. 7, carrier 302 is configured to retain four or less sample holders 304. For clarity, not all the through-holes In the illustrated embodiment shown in FIG. 5, each through-hole 309 has a diameter of about 320 micrometers, a thickness of about 300 micrometer, and a volume of about 33 nanoliters. Through-holes 309 have a nominal spacing in the illustrated embodiment of about 500 micrometers center to center. As discussed in greater detail below, optical system 100 may be configured to allow imaging and processing of biological samples contained in through-holes having such small diameters or volumes. Additionally or alternatively, system 1000 and/or optical system 100 is configured receive and process a sample holder 304 having smaller through-hole diameter and/or a smaller nominal spacing than in the illustrated embodiment of FIG. 5. For example, optical system 100 may be configured to allow system 1000 to receive and process a sample holder 304 comprising through-holes having a diameter that is less than or equal to 250 micrometer and/or a volume that is less than or equal to 5 nanoliters. Alternatively, optical system 100 may be configured to allow system 1000 to receive and process a sample holder 304 comprising through-holes having a diameter that is less than or equal to 150 micrometer and/or a volume that is less than or equal to one nanoliter.

In certain embodiments, an initial sample or solution for a sample holder, such as sample holders 204, 304, may be divided into hundreds, thousands, tens of thousands, hundreds of thousands, or even millions of reaction sites, each having a volume of, for example, a few nanoliters, about one nanoliter, or less than one nanoliter (e.g., 10's or 100's of picoliters or less).

In the illustrated embodiments shown in FIGS. 4 and 5, sample holders 204, 304 have a rectangular shape; however, other shapes may be used, such as a square or circular shape. In certain embodiments, a sample holder such as sample holder 304 has a square shape and an overall dimension of 15 millimeter by 15 millimeter. In such embodiments, the sample holder may have an active area, region, or zone with a dimension of 13 millimeter by 13 millimeter. As used herein, the terms "active area", "active region", or "active zone" mean a surface area, region, or zone of a sample holder, such as the sample holders 204 or 304, over which reaction regions, through-holes, or solution volumes are contained or distributed. In certain embodiments, the active area of sample holder 304 may be increased to 14 millimeter by 14 millimeter or larger, for example, a 15 millimeter by 15 millimeter substrate dimension.

In the illustrated embodiment of FIG. 5, through-holes 309 may have a characteristic diameter of 320 micrometer and a pitch of 500 micrometers between adjacent through-holes. In other embodiments, through-holes 309 have a characteristic diameter of 75 micrometer and have a pitch of 125 micrometers between adjacent through-holes. In yet other embodiments, through-holes 309 have a characteristic diameter of that is less than or equal 75 micrometers, for example, a characteristic diameter that is less or equal to 60 micrometers or less or equal to 50 micrometers. In other embodiments, through-holes 309 have a characteristic diameter that is less than or equal to 20 micrometers, less than or equal to 10 micrometers, or less than or equal to 1 micrometer. The pitch between through-holes may be less than or equal to 125 micrometers, for example, less than or equal to 100 micrometers, less than or equal to 30 micrometers, or less than or equal to 10 micrometers.

In certain embodiments, sample holder 304 comprises a substrate having a thickness between the opposing surfaces of sample holder 304 that is at or about 300 micrometer, wherein each through-hole 309 may have a volume of 1.3 nanoliter, 33 nanoliters, or somewhere between 1.3 nanoliter and 33 nanoliters. Alternatively, the volume of each through-holes 309 may be less than or equal to 1 nanoliter, for example, by decreasing the diameter of through-holes 309 and/or the thickness of sample holder 304 substrate. For example, each through-holes 309 may have a volume that is less than or equal to 1 nanoliter, less than or equal to 100 picoliters, less than or equal to 30 picoliters, or less than or equal to 10 picoliters. In other embodiments, the volume some or all of the through-holes 309 is in a range from 1 nanoliter to 20 nanoliters.

In certain embodiments, the density of through-holes 309 is at least 100 through-holes per square millimeter. Higher densities are also anticipated. For example, a density of through-holes 309 may be greater than or equal to 150 through-holes per square millimeter, greater than or equal to 200 through-holes per square millimeter, greater than or equal to 500 through-holes per square millimeter, greater than or equal to 1,000 through-holes per square millimeter, or greater than or equal to 10,000 through-holes per square millimeter.

Advantageously, all the through-holes 309 with an active area may be simultaneously imaged and analyzed by an optical system. In certain embodiments, active area comprises over 12,000 through-holes 309. In other embodiments, active area comprises at least 25,000, at least 30,000, at least 100,000, or at least 1,000,000 through-holes.

In certain embodiments, through-holes 309 comprise a first plurality of the through-holes characterized by a first characteristic diameter, thickness, or volume and a second plurality of the through-holes characterized by a second characteristic diameter, thickness, or volume that is different than the first characteristic diameter, thickness, or volume. Such variation in through-hole size or dimension may be used, for example, to simultaneously analyze two or more different nucleotide sequences that may have different concentrations. Additionally or alternatively, a variation in through-hole 104 size on a single substrate 304 may be used to increase the dynamic range of a process or experiment. For example, sample holder 304 may comprise two or more subarrays of through-holes 309, where each group is characterized by a diameter or thickness that is different a diameter or thickness of the through-holes 309 of the other or remaining group(s). Each group may be sized to provide a different dynamic range of number count of a target polynucleotide. The subarrays may be located on different parts of substrate 304 or may be interspersed so that two or more subarrays extend over the entire active area of sample holder 304 or over a common portion of active area of sample holder 304.

In certain embodiments, at least some of the through-holes 309 are tapered or chamfered over all or a portion of their walls. The use of a chamfer and/or a tapered through-holes have been found to reduce the average distance or total area between adjacent through-holes 309, without exceeding optical limitations for minimum spacing between solution sites or test samples. This results in a reduction in the amount liquid solution that is left behind on a surface of substrate 304 during a loading process. Thus, higher loading efficiency may be obtained, while still maintaining a larger effective spacing between adjacent solution sites or test samples for the optical system.

In certain embodiments, system 1000 is configured to receive and process different types or numbers of block 210, carrier 202, and/or sample holder 204. For example, Thus, system 1000 may be configured to receive and process different sample holders 204 having different numbers of wells 209. Thus, system 1000 may be configured to receive and process sample holders 204 containing 96 samples and sample holders 204 containing 48 wells and/or 384 well or/or more than 384 wells. Additionally or alternatively, system 1000 may be configured to receive and process different sample formats or container configurations. For examples, in addition to receiving a sample holder 204 comprising a predetermined number of wells, system 1000 may also be configured to receive and process one or more sample holders 304 comprising the plurality of through-holes 309. In certain embodiments, system 1000 is configured to receive and process four different types of sample holders. Some of the characteristics of wells or through-holes used in these four sample holders are listed in Table 1 below.

TABLE 1

Characteristics of four sample holders according to an embodiment of the present invention.

| Sample Holder | Sample Cell Type | Number of Cells | Characteristic Cell Volume | Characteristic Cell Diameter |
|---|---|---|---|---|
| A | Well | 96 | 200 microliters | 5 millimeters |
| B | Well | 384 | 50 microliters | 3 millimeters |
| C | Cavity | 384 | 2 microliters | 3 millimeters |
| D | Through-hole | 4 × 3072 | 0.033 microliters | 0.35 millimeters |

Referring again to FIGS. 1-3, optical sensor 118 may comprise one or more photodetectors or photosensors, for example, one or more photodiodes, photomultiplier tubes, or the like. Alternatively, optical sensor 118 may comprise a one-dimensional or two-dimensional photodetector array 164, such as a charge-coupled device (CCD), complementary metal-oxide-semiconductor (CMOS), or the like. In the illustrated embodiment in FIG. 1, photodetector array 164 comprises a two dimensional array of photosensitive pixels defining photosensitive surface upon which an optical image or signal may be formed by emission optical system 125.

Excitation source 110 may be a halogen lamp, a Xenon lamp, high-intensity discharge (HID) lamp, one or more light emitting diodes (LEDs), one or more laser, or the like. In certain embodiments, excitation source 110 comprises a plurality of light sources having different emission wavelength ranges to excite different fluorescent dyes in biological samples 115, for a example, a plurality of LED light sources having different colors or emission wavelength ranges. In such embodiments, excitation filter assembly 132 may be omitted or may be incorporated for use with at least some of the different light sources to further limit the wavelength range of light or radiation reaching samples 115.

In certain embodiments, excitation source 110 comprises one or more broadband or white light LED sources. For example, excitation source 110 may comprise a high power, broadband source having at least 5 watts of total output optical power, at least 10 watts of output optical power, or at least 25 watts of output optical power. In such embodiments, excitation filter assembly 132 may be incorporated to limit or define the spectral content of the radiation or light received by samples 115 and/or sample holder 204, 304. The spectral content of the broadband source 110 may be configured to favorably provide more energy over wavelength ranges that, for example, correspond to probes or dye molecules in samples 115 that are less efficient, are typically found lower concentrations, or otherwise require more photonic energy that other dyes contained in samples 115.

Figure 8:
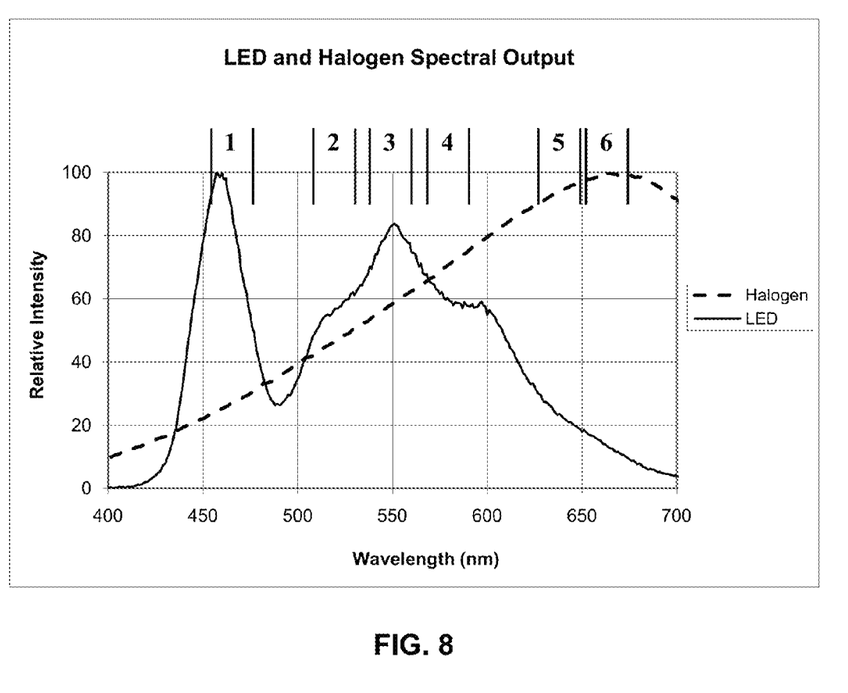
FIG. 8 is a graph showing the spectral output from an excitation source according to an embodiment of the present invention.

In a non-limiting example, in certain embodiments, excitation source 110 comprises a single broadband LED having a total optical power of greater than 10 watts over the spectral range produced by the LED. The spectral output characteristics of such an excitation source is shown by the solid line in the graphs shown in FIG. 8. The horizontal axis corresponds to the wavelength of radiation emitted by the LED excitation source 110, while the vertical axis is a relative output intensity. The "relative intensity" for the plot in FIG. 8 is a percentage value that is defined as 100 times the intensity measured at a given wavelength divided by the maximum intensity measured at any wavelength within range of wavelengths produced by the LED. For example, according to the plot in FIG. 8, the measured intensity out of the LED at a wavelength of 450 nanometer is about 80 percent of the maximum intensity, where the maximum measured intensity occurs at an output wavelength of 457 nanometers. By way of comparison, similar data for a halogen lamp used in a prior art system is also shown in FIG. 8 as dashed lines. The sets of double lines with numeral in between indicate the approximate transmission wavelength bands for the excitation filters shown in FIG. 3.

For the illustrated embodiment shown in Table 1, the characteristic cell diameter and volume of sample holder D is much smaller than that of sample holders A-C. As a result, a typical fluorescence signal produced by sample holder D is much smaller than a typical fluorescence signal produced by sample holders A-C under similar conditions, for example, when using biological samples containing similar concentrations of a biological test sample and/or a fluorescent probe or reference dye. For these reasons, the halogen excitation source shown in FIG. 8 may not provide sufficient intensity or power density for fluorescent probes or dyes excited by light in the wavelength range provided by filters 1-3 in FIG. 3.

In certain embodiments, fluorescent probes or dyes excited by light in the wavelength range provided by excitation filters 1, 2, and 4 in FIG. 3 are either more commonly used or are of greater importance than those excited by light in the wavelength range provided by filters 3, 5, and/or 6, for example, in the wavelength range provided by either filters 5 or 6. For example, in certain embodiments, the dyes FAM™ VIC®, and ROX™ are used, which dyes are commercially available from Life Technologies in Carlsbad, Calif. In such embodiments, excitation filter 1 is used to excite the dye FAM™, excitation filter 2 may be used to excite the dye VIC®, and excitation filter 4 may be used to excite the dye ROX™. Additionally or alternatively, it may be that fluorescent probes or dyes excited by light in the wavelength range provided by filters 3, 5, and/or 6 are not used with all types of sample holders A-D and/or with all types of sample holders 204, 304, for example, are not used with sample holders D and/or sample holder 304. In such embodiments as these, an excitation source 110 comprising an LED source having spectral characteristics the same or similar to those shown in FIG. 8 has an unexpected benefit, even though (1) the spectral power or intensity of the LED source for fluorescent probes or dyes excited by light in the wavelength range provided by filters 5 and 6 is less than that for the halogen source shown in FIG. 8, and (2) the spectral power or intensity of the LED source for fluorescent probes or dyes excited by light in the wavelength range provided by filters 5 and 6 is less than that for fluorescent probes or dyes excited by light in the wavelength range provided by filters 1, 2, and/or 4. It has been discovered that, due to the relatively large sample volumes provided by the sample cells in sample holders A-C, an LED source such as that characterized in FIG. 8 is able to provide enough excitation energy to the biological samples so that system 1000 is able to process the signals or images received by optical sensor 118.

Accordingly, it has been discovered that instrument or system 1000 can process biological samples to provide useful data using a broadband LED that produces light or radiation having a maximum intensity and/or power density at a wavelength that is less than 600 nanometers and/or that is less than 550 nanometers. For example, instrument or system 1000 can provide useful PCR data (e.g., qPCR and/or dPCR data) using such a broadband LED, such as that represented in FIG. 8. The result is an instrument that can provide data, such as PCR data, over a wide range of sample sizes and sample holder or cell formats, for example, all the sample sizes and sample cell formats listed in Table 1.

In certain embodiments, system 1000 includes an excitation source 110 comprising an LED having a spectral profile characterized by a maximum intensity or optical output power at a wavelength that is less than 550 or 600 nanometers and an intensity or optical output power that is less than 50 percent the maximum value at a wavelength of 650 nanometer and/or 670 nanometers. In other embodiments, system 1000 includes an excitation source 110 comprising an LED having a spectral profile characterized by a maximum intensity or optical output power at a wavelength that is less than 550 or 600 nanometers and an intensity or optical output power that is less than 30 percent or less than 20 percent the maximum value at a wavelength of 650 nanometer and/or 670 nanometers. In certain embodiments, the system 1000 further comprise an emission optical system 125 that is able to provide useful biological data (e.g., PCR data) for sample cells having a diameter of less than 500 micrometer, less than 200 micrometers, or less than 100 micrometers that contain fluorescent probes or dye molecule that fluoresce at excitation wavelengths that are less than or equal to 560 nanometer, while also being able to provide useful biological data (e.g., PCR data) for sample cells having a diameter of greater than 2 millimeters or greater than 3 millimeters that contain fluorescent probes or dye molecule that fluoresce at excitation wavelengths that are greater than or equal to 620 nanometer or greater than or equal to 650 nanometers.

When used an system 1000 according to embodiments of the present invention, another unexpected advantage of an LED as described in the previous paragraph and/or as illustrated in FIG. 8 is that infrared (IR) emissions from excitation source 110 are much lower than, for example, a halogen light source according to that shown in FIG. 8. Thus, embodiments of the present invention provide reduced IR noise without the need extra optical element such as so-called "hot mirrors" to block IR emissions.

In certain embodiments, the output intensity, power, or energy of excitation source 110 may be varied depending on a condition or variable value, for example, depending on the type of sample holder used, size of one or more reaction regions, experiment or run conditions of system or instrument 1000, experiment or run conditions of optical system 100, experiment or run conditions of sample processing system 200, or the like. For example, excitation source 110 may be an LED light source in which the output intensity, power, or energy is varied depending on one or more of the conditions and/or variable values. In such embodiments, the output intensity, power, or energy of the LED may be varied by adjusting or changing a current or voltage driving the LED, and/or by adjusting or changing a duty cycle of the LED. In certain embodiments, the output intensity, power, or energy of excitation source 110 is changed depending on the type of sample holder being used in system 1000. For example, in certain embodiments, excitation source 110 may be an LED that is run at full output power, intensity, or energy—or at a higher power setting output power, intensity, or energy—when sample holder A from Table 1 is used. By contrast, the LED may be run at a lower output power, intensity, or energy when a different sample holder is used, for example, sample holder B, C, or D from Table 1 is used. Such an arrangement allows system 1000 to provide emission data for the smaller sample volume sizes and/or lower sample concentrations that occur when sample hold A is used, while also avoiding a saturation of optical sensor 118 when other larger sample volumes and/or higher sample concentrations are used.

Lens 152 is configured to form an image on photodetector array 164, for example, by focusing collimated radiation entering from a particular direction to a spot or point, for example, to a diffraction limited spot or a nearly diffraction limited spot. Lens 152 may be a simple lens, such as a plano-convex lens, plano-concave lens, bi-convex lens, bi-concave lens, meniscus lens, or the like. Alternatively, lens 152 may comprise a compound lens such as a doublet lens or triplet lens that may, for example, comprise different lens materials selected to correct or reduce a chromatic aberration. In other embodiments, lens 152 comprises system of lenses such as a camera lens system or microscope objective, for example, a commercially available camera lens. The camera lens system may be a commercially available camera lens comprising a conventional lens system design, for example, a double Gauss design, a Cooke triplet design, retrofocus lens design (e.g., Distagon lens design), a Tessar lens design, or the like.

Lens 154 may be a single field lens, for example, configured to provide a telecentric optical system when combined with the remaining optical elements of excitation optical system 120 and/or emission optical system 125. In such embodiments, lens 154 may be a simple lens, such as a plano-convex lens, plano-concave lens, bi-convex lens, bi-concave lens, meniscus lens, or the like. Alternatively, lens 152 may comprise a doublet lens or triplet lens, for example, comprising different lens material to correct for a chromatic aberration. Additionally or alternatively, lens 154 may comprise a Fresnel lens or a diffractive optical element, surface, or pattern. In certain embodiments, lens 154 may comprise a lens system, for example, a field lens in combination with an additional lens or lenslet array configured to focus light within a sample well of sample holder 204. The lenslet array may comprise a Fresnel lens or a diffractive optical element, surface, or pattern. Examples of such lens configurations are also describe in U.S. Pat. No. 6,818,437, which is herein incorporated by reference in its entirety as if fully set forth herein.

Figure 9:
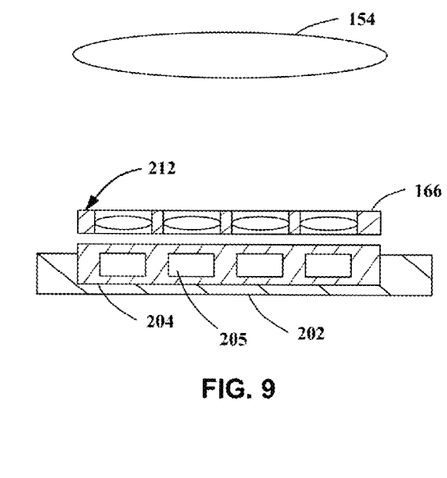
FIG. 9 is a cross-sectional view of a heated lid, sample holder, and carrier according on an embodiment of the present invention.
Figure 10:
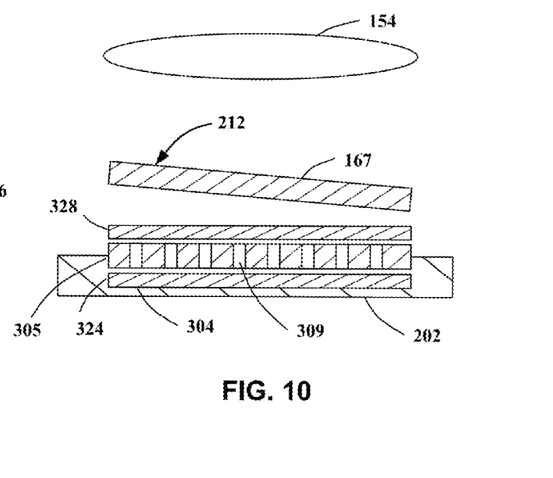
FIG. 10 is a cross-sectional view of a heated lid, sample holder, and carrier according on another embodiment of the present invention.

Referring to FIG. 9, in certain embodiments, heated lid 212 comprises a lenslet array 166, for example, for use with sample holder 204 (e.g., like sample holders A-C listed in Table 1) for focusing light from excitation beam 111 into a well or cavity of a sample holder, such as sample holders 204 in the illustrated embodiment. With additional reference to FIG. 10, heated lid 212 may additionally or alternatively comprise an optical window 167 for providing thermal isolation or improved thermal performance of the thermal environment in or around a sample holder, such as sample holder 304 in the illustrated embodiment. In certain embodiments, convective current can be produced when window 167 is not located as shown in FIG. 10. Such convective heat flow has been found to result in higher temperature or thermal non-uniformity (TNU) in substrate 306, in sample holder 304, and/or between samples 315 than may be acceptable in some applications. Accordingly, placement of window 167 between lens 154 and sample holder 304 can decrease the amount of convective currents around sample holder 304 and lead to a decreases in TNU.

Optical window 167 may be used in addition to or in place of optical window 162 shown in FIG. 1. Either or both windows 162, 167 may be disposed parallel to a surface of sample holder 304 and/or perpendicular to optical axis 170. Alternatively, one or both windows 162, 167 may be disposed at an angle relative to a surface of sample holder 304 and/or at an acute angle to optical axis 170, for example, to reduce retro-reflections of light from excitation beam 111 back toward optical sensor 118. One or both windows 162, 167 may comprise an antireflective coating to reduce retro-reflections of light from excitation beam 111 back toward optical sensor 118. The antireflective coating may be used in addition to, or as an alternative to, tilting one or both windows 162, 167. Thus, system 1000 is able to accommodate and provide useful biological data (e.g., PCR data) for sample holders having a diversity of optical requirements by providing heated lids 212 having different optical characteristics from one another and/or serving differing thermal requirements for sample holders, such as sample holders 204, 304 (e.g., sample holders A-D listed in Table 1).

In certain embodiments, the combination of lenses or lens systems 152, 154 is selected to provide a predetermined optical result or image quality. For example, in order to reduce system cost or to simplify the emission optical system 125 design, lens 152 may comprise a commercially available camera lens. Such lenses can provide very high image quality (e.g., images with low chromatic and monochromatic aberration) under certain viewing conditions. However, the careful balance of higher order aberrations incorporated into such camera lens design used to provide such high image quality can be disturbed with the introduction of other lenses into an imaging system. For example, in the illustrated embodiment shown in FIG. 1, a field lens such as lens 154 is added to emission optical system 125. Lens 154 is common to both excitation optical system 111 and emission optical system 125 to provide both a generally more compact optical system and efficient transfer of fluorescent energy from a sample to the detection system.

In prior art systems, a field lens having a plano-convex lens shape or figure has been found to provide certain favorable characteristic in this respect, for example, to provide a telecentric lens system configured to provide even illumination over a large field of view. However, to provide an acceptably low level of optical aberrations, such prior art systems also incorporate a custom camera lens design in order to reduce overall system aberrations when used in combination the plano-convex field lens. In particular, due to the extended field of view used to simultaneously image a large number of biological samples, the camera lens was designed to provide low amounts of field curvature. However, it has been discovered that the combination of a plano-convex lens with a conventional or commercially available camera lens can result in large amounts of field curvature that are undesirable. It has been further discovered that field curvature can be significantly reduced by combining a biconvex field lens 154 with a conventional or commercially available camera lens, as illustrated in FIG. 1. This result is surprising, since a biconvex lens would normally be expected to reduce overall image quality in a telecentric lens system. For example, it has been found that when lens 152 comprises a commercially available camera lens of a retro-focus design (e.g., a Distagon lens design), the amount of field curvature produced when field lens 154 is a biconvex lens is much smaller than the amount of field curvature produced when field lens 154 is a plano-convex lens.

Emission filter assembly 130 may comprise a first filter module 138 characterized by a first optical power and a first filter 140 having a first filter function or transmission range 140a. In the illustrated embodiment, first filter function 140a is shown as filter number 6 in the table of FIG. 2 and is characterized by a first low-pass wavelength 140L of 700 nanometers and a first high-pass wavelength 140H of 720 nm, so that light within this wavelength range is transmitted, or largely transmitted, through the first filter 140, while light or other electromagnetic radiation outside this wavelength range is blocked, or substantially blocked, by first filter 140. The wavelengths listed in FIGS. 2 and 3 may represent the wavelengths at which the transmission of a filter is one-half the maximum transmission of the filter over the transmission wavelength range. In such cases, the difference between high-pass wavelength and the low-pass wavelength define a full width at half maximum transmission (FWHM) range.

Emission filter assembly 130 also includes a second, and optionally a third, filter component, element, or module 142, 143. Second and third filter modules 142, 143 are characterized by second and third filters 145, 146 having a second and third filter functions or transmission ranges 145a, 146a. Either or both filter modules 142, 143 may have an optical power that is the same as, or different from, the optical power of first filter module 138. At least one of the filter modules 142, 143 may have an optical power of zero, which power may in general be either positive or negative. Filter functions 145a, 146a comprise second and third low-pass wavelengths 145L, 146L second and third high-pass wavelengths 145H, 146H, respectively, for example, as filter numbers 1 and 5 in the table of FIG. 2. Second and third low-pass wavelengths 145L, 146L may be different than the low-pass wavelength 140L and/or may be different from one another. Similarly, second and third high-pass wavelengths 145H, 146H may be different than the high-pass wavelength 140H and/or may be different from one another. In the illustrated embodiment, the transmission wavelength bands for filters 140, 145, 146 (wavelengths 140L to 140H, 145L to 145H, and 146L to 146H) do not overlap; however, in other embodiments, there may be at least some overlap in the wavelength bands between two or more of the filters in emission filter assembly 130. In certain embodiments, one or more of functions 140a, 145a, 146a may comprise a function that is different than the simple bandpass configuration illustrated in FIG. 2.

FIG. 3 illustrates various filters available for use with excitation filter assembly 132. In FIG. 1, excitation filter assembly 132 comprises three filters, for example, filters 1, 2, and 6 in FIG. 3, which in use may correspond to filters 1, 2, and 6 shown in FIG. 2 for emission filter assembly 130. At least some of the filter modules 133 of excitation filter assembly 132 may have non-zero optical powers, which power may in general be either positive or negative. Alternatively, all the filter modules 133 may have zero or about zero optical power. In certain embodiments, selection of a particular filter module 133 is associated with a particular filter module 131 of filter assembly 130. Alternatively, filter modules 133, 131 may be selected independently of one another.

In the illustrated embodiment shown in FIG. 1, only three filter modules are shown for each filter assembly 130, 132; however, either or both filter assemblies may comprise more or less than three filter modules. For example, FIGS. 2 and 3 each show a total of 6 filters, each of which filters may be associated an optical power (not shown). In certain embodiment, either or both filter assemblies 130, 132 contain all six filters shown in the table shown in FIGS. 2 and 3, respectively. Alternatively, either or both filter assemblies 130, 132 may comprise less than six filters.

Filter functions 145a, 146a comprise respective second low-pass wavelengths 145L, 146L that may be different than the first low-pass wavelength 140L and may be different from one another. Each filter of the filters in emission filter assembly 130 or in excitation filter assembly 132 may comprise a transmission range of electromagnetic radiation or light that is different and non-overlapping from the remaining filters of filter assembly 130 or filter assembly 132. Alternatively, two or more of the filters in filter assembly 130 or in filter assembly 132 may comprise transmission ranges of electromagnetic radiation or light that at least partially overlap one another.

In certain embodiments, the optical power one more or more of filter modules 131, or of each filter modules 133, is selected to compensate for or reduce an optical aberration of the remaining optical elements of emission optical system 125 or excitation optical system 120 over a wavelength range of the filter being used. For example, in order to provide a predetermined image resolution or quality for various of the filter modules 131 at an image plane of optical sensor 118 or emission optical system 125, the optical powers of some or all of filter modules 131 may be selected to compensate for or reduce a chromatic or sphero-chromatic aberration introduced by emission optical system 125 over different filter wavelength ranges. Additionally or alternatively, one or more of filter modules 131 or of filter modules 133 may comprise a monochromatic aberration, such as spherical aberration, astigmatism, or coma, that is configured to alter, adjust, or reduce an overall aberration of emission optical system 125 or excitation optical system 120.

In certain embodiments, the optical power or a monochromatic aberration of one or more of filter modules 131 is configured to at least partially correct or adjust an image or focus of sample holder 204 and/or of at least some of the biological samples 115 in an image plane at or near a detection surface of optical sensor 118. For example, in the illustrated embodiment, the optical powers of filter modules 138, 142, 143 are all different from one another, with third filter module 143 having an optical power of zero or about zero. The optical power of filter modules 138, 142 may be selected so that an effective focal length of emission optical system 125 is adjusted over the transmission wavelength range of each filter 138, 142 is the same or about the same as the effective focal length when filter 143 is located in the emission optical system 125. Additionally or alternatively, the optical power of filter modules 138, 142 may be selected so that the image quality produced when corresponding filter 140, 145 is inserted into emission optical system 125 is the same or similar to the image quality produced when filter 146 is inserted into emission optical system 125. For example, the optical power for each filter module 131 may be selected so that images of biological samples 115 are the same size, or about the same size, for each filter module 138, 142, 143. Additionally or alternatively, the optical power for each filter module 131 may be selected so that a magnification and/or aberration of images of biological samples 115 are the same, or about the same, for each filter module 131. In certain embodiments, two or more of the optical powers may be the equal to one another. In general filter modules 138 and/or 142 may have optical powers that are greater than zero or less than zero in order to provide a desired correction or adjustment to the emission optical system 125 and/or images produced therefrom.

Beamsplitter 160 may be configured to selectively reflect a large amount of emitted light or radiation from excitation source 110 that is transmitted through a selected excitation filter module 133 and then directed toward sample holder 204, 304. For example, the coated beamsplitter 160 may comprise a dichroic reflector that is configured to reflect at least 95 percent or at least 99 percent of incident light transmitted through excitation filter module 133. The same coating for beamsplitter 160 can additionally be configured to transmit a large amount of emission light or radiation from biological samples 115, for example, to transmit at least 90 percent or at least 95 percent of light or radiation emitted by biological samples 115. In certain embodiments, a different beamsplitter 160 is associated with each different filter module 133, for example, by attaching the different beamsplitters 160 to excitation filter assembly 132. In certain embodiments, only some of the beamsplitters 160 are wavelength selective or dichroic beamsplitters, while others of beamsplitters 160 associated with some of excitation filter modules 133 are not wavelength selective, for example, a 50/50 beamsplitter that reflect 50 percent of incident radiation over a broad band of wavelengths. In such embodiments, excitation light or radiation not reflected by a beamsplitter 160, but transmitted through the beamsplitter 160, may be intercepted by an emission filter module 131 and directed to optical sensor 118 in the form of noise.

In certain embodiments, noise from excitation light or radiation transmitted through a beamsplitter 160 is reduced by reducing the size of the corresponding emission filter module 131. However, the size reduction of the corresponding emission filter module 133 may be limited so as to avoid loss of signal from at least some of the biological samples 115, 315, for example, due to vignetting effects on the more peripherally located samples. It has been discovered that a reduction in excitation radiation noise can be accomplished without significant loss of emission radiation signal by configuring the emission filters to have a shape that is the same as, or similar to, the shape of the area of sample holder 204, 304 containing samples 115, 315. For example, it can be seen in FIG. 4, 5, or 7 that a rectangular area is defined by an active area over which one or more of sample holders 204, 304 contain samples or sample cells within the field of view of optical sensor 118. In such cases, it has been found that a rectangular shaped emission filter 140, 145, 146 or emission filter module 138, 142, 143 provides reduced noise from excitation radiation transmitted through beamsplitter 160, without a significant loss of emission signal from samples 115, 315 or uneven illumination from samples over the entire area of sample holders 204, 304. In certain embodiments, the rectangular emission filter 140, 145, 146 or emission filter module 138, 142, 143 has the same, or a similar, aspect ratio as that defined by an active area of sample holders 204, 304, by carriers 202, 302, or by area of samples 115, 315 that are within the field of view or field of regard of optical sensor 118. For example, the aspect ratio of a rectangular emission filter (e.g., filter 140, 145, and/or 146) or filter module (e.g., filter module 138, 142, or 143) may be selected to be within 1 percent, 5 percent, 10 percent, or 20 percent of the aspect ratio of the active area of a sample holder (e.g., sample holders 204 or 304) or of a group of sample holders (e.g., the four sample holders 304 shown in FIG. 7).

During operation, biological samples 115 are disposed in a sample holder, for example in sample holder 204, sample holder 304, or the like. Biological samples 115 may include one or more nucleotide sequences, amino acid sequences, or other biological macromolecules including, but not limited to, oligonucleotides, genes, DNA sequences, RNA sequences, polypeptides, proteins, enzymes, or the like. In addition, biological samples 115 may include other molecules for controlling or monitoring a biological reaction including, but not limited to, primers, hybridization probes, reporter probes, quencher molecules, molecular beacons, fluorescent dyes, chemical buffers, enzymes, detergents, or the like. Additionally or alternatively, biological samples 115 may include one or more genomes, cells, cellular nucleuses, or the like.

Once the biological samples are loaded, one or more sample holders are loaded or mounted within system 1000. In the illustrated embodiment shown in FIG. 1, one or more sample holders are mounted in to carrier 202 or 302, which in turn is received by block 210 system 1000 and may be subsequently covered or secured by heated lid 212. As discussed above herein, block 210 and heated lid 212 may be removably mounted or secured within system 1000, for example, so either or both may be exchanged for another block or heated lid that is configured for use with a particular sample holder or carrier. Once the sample holder has been received by sample processing system 200, optical system 100 is used to monitor or measure one or more biological reactions or processes.

Emission optical system 125 of optical system 100 comprises an optical axis 170. A first emission beam 172 of emission beams 119 is emitted by a first biological sample located at or near optical axis 170. First emission beam 172 passes through emission optical system 125 such that at least a portion of the electromagnetic radiation from the sample produces a first sample image 173 at or near photodetector array 164 that is on or near optical axis 170. A second emission beam 174 of emission beams 119 is simultaneously emitted by second biological sample located at or near an outer edge location of the array of biological samples 115. Second emission beam 174 also passes through emission optical system 125 such that at least a portion of the electromagnetic radiation from the sample produces a second sample image 175 at or near optical sensor 118 that is displace from optical axis 170. Emission beams 172, 174 may be fluorescence beams produced by different probe molecules contained in the two respective samples in response to excitation beam 111. Depending upon the particular excitation filter module 133 selected, emission beams 172, 174 have a wavelength or wavelength range corresponding to the particular probe molecule that is excited by radiation from excitation beam 111 that is transmitted by the selected excitation filter module 133. For example, when filter number 1 in FIG. 3 may be used to filter radiation from excitation beam 111 and used in combination with emission filter number 1 in FIG. 2 (filter 146 of filter module 143 in FIG. 1) to transmit radiation from emission beams 172, 174 onto photodetector array 164. As discussed above herein, the combination of lenses 152, 154 may be selected to form images from emission beams 172, 174 that is low in monochromatic aberrations, and in particular has a low amount of field curvature. A lateral distance (e.g., in a direction normal to optical axis 170) between the first and second samples may be compared to a lateral distance between the corresponding images produced by emission optical system 125 to determine a transverse magnification for the system when filter 146 is being used.

In certain embodiments, for radiation within the transmission range of emission filter 146, first and second beams 172, 174 are collimated or nearly collimated when they leave lens 154 and form images at or near photodetector array 164 that have relatively low monochromatic aberrations and define a base system magnification. During use, emission filter assembly 130 may be subsequently moved (e.g., translated or rotated) so that emission filter module 143 and filter 146 are replaced by emission filter module 138 and filter 140 so the filter 140 (filter number 6 in FIG. 2) now becomes part of the emission optical system 125, as illustrated in FIG. 1. Optionally, excitation filter number 1 in FIG. 3 may also be replaced with excitation filter number 6 along excitation beam path 111. As a result of chromatic aberrations, for radiation within the transmission range of emission filter 140, first and second beams 172, 174 are no collimated, but are divergent when they leave lens 154. Thus, beams 172, 174 form images 173, 175 at or near photodetector array 164 that are further away from a principal plane of lens 152 than the images formed when filter 146 is present in emission optical system 125. To correct or compensate for this effective change in focal length of emission optical system 125 over the transmission wavelength range of filter 140, a lens or optic 178 with a net positive optical power is included in filter module 138.

The added optical power to filter module 140 and emission optical system 125 may be provided by a singlet lens 178, as shown in the illustrated embodiment of FIG. 1. The lens may be a plano-convex lens, plano-concave lens, bi-convex lens, bi-concave lens, meniscus lens, or the like. Alternatively, lens 178 may comprise a compound lens such as a doublet lens or triplet lens that may, for example, comprise different lens materials selected to correct or reduce a chromatic aberration. Optic 178 may additionally or alternatively comprise a diffractive optical element. Optic 178 may be either a separate optical element, as shown in FIG. 1, or combined with filter 140 to form a single element. For example, optic 178 and filter 140 may be bonded together along a common optical face. Alternatively, optic 178 and filter 140 be formed together from a single substrate, for example, formed from a filter material having one or both optical surfaces that are curved and/or contain a diffractive optical pattern. In certain embodiments, optic 178 is located in a different part of emission optical system 125 than shown in FIG. 1, for example, on or proximal lens 154, window 162, or beamsplitter 160, or at a location between beamsplitter 160 and emission filter assembly 130.

In addition to changing the effective focal length of emission optical system 125, filter 140 may also result in a change in transverse magnification for the system. For example, even when lens 178 is included in filter module 138, the lateral distance between images 173, 175 may be different when filter module 138 is used than when filter module 143 is used. In addition, the change from filter module 143 to filter module 140 may introduce or alter various monochromatic aberration of emission optical system 125, for example, a spherical aberration and/or field curvature. Accordingly, optic 178 or filter module 138 may be configured to at least partially correct or compensate for such differences or changes in magnification and/or in one or more monochromatic aberrations relative to when filter module 143 is used. In certain embodiments, system 1000 or electronic processor 300 may include image processing instructions to at least partially correct or compensate for changes in magnification and/or in one or more monochromatic aberrations introduced by the use of filter module 138 into emission optical system 125. The image processing instructions may be used in combination with, or in place of, corrective optic 178 to at least partially correct or compensate for changes in produces by the use of filter 140 in place of filter 146, including changes in effective system focal length, magnification, chromatic aberrations, and/or one or more monochromatic aberrations such as defocus, spherical aberrations, or field curvature.

In certain embodiments, each filter module 131 is disposed, in its turn, along the emission optical path 128 at a location where emission beam 119, or some portion thereof, is either diverging or converging, whereby one or more of filter modules 138, 142, 143 alters the amount of divergence or convergence to correct or adjust an effective focal length of emission optical system 125 and/or a spot size at an image plane of emission optical system 125. In such embodiments, an optical power of at least one of filter modules 138, 142, 143 is non-zero (i.e., either positive or negative) over at least the transmission wavelength range or filter function of corresponding filter 138, 142, 143.

In certain embodiments, the optical power of one or more of filter modules 131, or one or more of filter modules 133, is greater than zero and less than one Diopter. For example, the optical power of one or more of filter modules 131, or one or more of filter modules 133, is greater than zero and less than or equal to one-third of one Diopter, less than or equal to one-quarter of one Diopter, or less than or equal to one-eighth of one Diopter. Thus, optical power adjustment, while greater than zero, may be relatively small, so that only sight adjustments are made in the optical characteristics of the emission optical system 125 for at least some of the filters 140, 145, 146. Such slight adjustment in optical power in the emission optical system 125 for different filters have been found to provide important optical corrections, resulting images created at optical sensor 118 that allow for better comparison between image data at different excitation and emission conditions.

While most of the discussion above has related to emission optical system 125 and the associated filter module 131, it will be appreciated that embodiments of the present invention also encompass similar treatment, where appropriate, of excitation optical system 120 and the associated filter module 133.

In the illustrated embodiment shown in FIG. 1, a non-zero optical power for some of filter module 131, 133 is provided by a separate lens. Alternatively, a filter module 131, 133 may comprise a single optical element having both an optical power and filter transmission function. In certain embodiments, the single optic is made of a single material. Alternatively, two or more materials or elements may be adhered, joined, or bond together to form a filter module. In certain embodiments, the optical power may be provided by a diffractive or holographic optical element or surface. The diffractive or holographic element or surface may be configured to reduce the size or thickness of a filter module. Additionally or alternatively, the diffractive or holographic element or surface may be configured to introduce a chromatic aberration that is used to reduce a chromatic aberration produced by the remaining elements of optical systems 125 or 120. In yet other embodiments, one or more of filter assemblies comprises a Fresnel lens or a curved mirror.

In certain embodiments, filter assembly 130 and/or 132 comprise a carrousel configuration in which different filter modules 131 or 133 are rotated into and out of the emission optical path 128 or excitation optical path 126, respectively. In certain embodiments, filter assembly 130 and/or 132 comprises interchangeable optical elements having differing optical powers and interchangeable filters having differing filter functions, wherein the optical elements and filters are independently selectable from one another.

First optical element 152 is disposed near the optical sensor and is configured to provide images of samples 115 and/or sample holder 200. First optic element 152 may be a simple lens, such as a plano-convex or bi-convex lens, or a commercially available camera lens, such as a Double Gauss lens, Distagon lens, Angenieux retrofocus lens, Cooke triplet, or the like. In the illustrated embodiment, filter modules 131 are located between beamsplitter 160 and optical element 152, proximal optical element 152. Second optical element 154 may be located near sample holder 200 and be configured to provide a telecentric optical system for illumination of the plurality of biological samples 115.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

The following list of co-pending U.S. applications are herein incorporated by reference in their entirely as if fully set forth herein:

U.S. Provisional Patent Application No. 61/541,453, filed on Sep. 30, 2011.
U.S. Provisional Patent Application No. 61/541,515, filed on Sep. 30, 2011.
U.S. Provisional Patent Application No. 61/541,342, filed on Sep. 30, 2011.
U.S. Design Patent Application No. 29/403,049, filed on Sep. 30, 2011.
U.S. Design Patent Application No. 29/403,059, filed on Sep. 30, 2011.
U.S. Provisional Patent Application No. 61/541,495, filed on Sep. 30, 2011.
U.S. Provisional Patent Application No. 61/541,366, filed on Sep. 30, 2011.
U.S. Provisional Patent Application No. 61/541,371, filed on Sep. 30, 2011.
U.S. Provisional Patent Application No. 61/564,027, filed on Nov. 28, 2011.
U.S. Provisional Patent Application No. 61/660,343, filed Jun. 15, 2012.

What is claimed is:

1. An instrument for biological analysis, comprising:
an excitation source producing electromagnetic radiation;
a sample holder configured to receive a plurality of biological samples;
an optical sensor configured to receive an emission from the biological samples;
an excitation optical system disposed along an excitation optical path and configured to direct the electromagnetic radiation from the excitation source to the biological samples;
an emission optical system disposed along an emission optical path and configured to direct electromagnetic emissions from the biological samples to the optical sensor;
a filter assembly comprising a plurality of filter components, the plurality of filter components comprising:
a first filter component having no optical power, the first filter component consisting of a first filter characterized by at least one of (a) a first low-pass wavelength or (b) a first high-pass wavelength;
a second filter component characterized by a finite focal length, the second filter comprising a singlet lens and a second filter characterized by at least one of (a) a second low-pass wavelength that is different than the first low-pass wavelength or (b) a second high-pass wavelength that is different than the first high-pass wavelength;
wherein the filter assembly selectively locates the plurality of filter components into the emission optical path;
wherein the singlet lens changes an effective focal length of the emission optical system and a magnification of the emission optical system.

2. The instrument of claim 1, wherein the plurality of filter components includes a third filter component comprising a third optical power and a third filter function.

3. The instrument of claim 1, wherein the plurality of filter components has a first condition in which the first filter component is disposed along the emission optical path and a second condition in which second filter component is disposed along the emission optical path, the optical power being sufficient to at least partially compensate for an aberration introduced by the second filter.

4. The instrument of claim 3, wherein the aberration is a chromatic aberration.

5. The instrument of claim 1, further comprising a first lens element and a second lens element, the lens elements having positive optical power and disposed along the emission optical path, the first lens element disposed between the optical sensor and one of the filter component, the second lens element disposed between the one of the filter components and the sample holder.

6. The instrument of claim 5, wherein the second lens element is disposed along the excitation optical path.

7. The instrument of claim 5, further comprising a beamsplitter disposed along the emission optical path, the second lens element and the beamsplitter disposed along the excitation optical path.

8. The instrument of claim 1, wherein the optical sensor comprises a charge coupled device CCD detector array or a complementary metal-oxide-semiconductor CMOS detector array comprising at least 4,000,000 pixels.

9. The instrument of claim 1, wherein the instrument is a real-time polymerase chain reaction (qPCR) instrument.

10. The instrument of claim 1, further comprising a thermal control unit configured to control the temperature of the biological samples.

* * * * *